(12) United States Patent
Brezinski et al.

(10) Patent No.: US 9,506,740 B2
(45) Date of Patent: Nov. 29, 2016

(54) SYSTEM AND METHOD FOR CALIBRATED SPECTRAL DOMAIN OPTICAL COHERENCE TOMOGRAPHY AND LOW COHERENCE INTERFEROMETRY

(75) Inventors: Mark Brezinski, Marblehead, MA (US); Bin Liu, Chestnut Hill, MA (US); Ehsan Azimi, Baltimore, MD (US)

(73) Assignee: The Brigham and Women's Hospital, Boston, MA (US)

( * ) Notice: Subject to any disclaimer, the term of this patent is extended or adjusted under 35 U.S.C. 154(b) by 982 days.

(21) Appl. No.: 13/513,052

(22) PCT Filed: Dec. 1, 2010

(86) PCT No.: PCT/US2010/058548
§ 371 (c)(1),
(2), (4) Date: Mar. 25, 2013

(87) PCT Pub. No.: WO2011/068862
PCT Pub. Date: Jun. 9, 2011

(65) Prior Publication Data
US 2013/0182259 A1    Jul. 18, 2013

Related U.S. Application Data

(60) Provisional application No. 61/265,571, filed on Dec. 1, 2009.

(51) Int. Cl.
*G01B 11/02* (2006.01)
*G01B 9/02* (2006.01)
(Continued)

(52) U.S. Cl.
CPC ......... *G01B 9/02091* (2013.01); *A61B 5/0066* (2013.01); *G01B 9/02044* (2013.01);
(Continued)

(58) Field of Classification Search
CPC .......... G01B 9/02091; G01B 9/02044; G01B 9/02074; A61B 5/0066; A61B 5/7257; G01N 21/4795; G01N 2021/1787
USPC ........................................................ 356/456
See application file for complete search history.

(56) References Cited

U.S. PATENT DOCUMENTS

| 7,359,062 B2 | 4/2008 | Chen et al. |
| 2007/0268456 A1 | 11/2007 | Ohbayshi et al. |
| 2008/0037608 A1 | 2/2008 | Zhou et al. |

FOREIGN PATENT DOCUMENTS

| JP | 2007-101365 A | 4/2007 |
| JP | 2007-298461 A | 11/2007 |

OTHER PUBLICATIONS

International Search Report and Written Opinion under date of mailing of Aug. 9, 2011 in connection with PCT/US2010/058548.

*Primary Examiner* — Tarifur Chowdhury
*Assistant Examiner* — Jonathon Cook
(74) *Attorney, Agent, or Firm* — Quarles & Brady LLP

(57) ABSTRACT

Systems and methods for enhancing spectral domain optical coherence tomography (OCT] are provided. In particular, a system and method for calibration of spectral interference signals using an acquired calibration signal are provided. The calibration signal may be logarithmically amplified to further improve the accuracy of the calibration. From the calibration signal, a series of more accurate calibration data are calculated. An acquired spectral interference signal is calibrated using these calibration data. Moreover, systems that include logarithmic amplification of the spectral interference signal and variable band-pass filtering of the spectral interference signal are provided. Such systems increase the dynamic range and visualization capabilities relative to conventional spectral domain OCT systems.

40 Claims, 10 Drawing Sheets

(51) Int. Cl.
*A61B 5/00* (2006.01)
*G01N 21/47* (2006.01)
*G01N 21/17* (2006.01)

(52) U.S. Cl.
CPC ....... *G01B9/02074* (2013.01); *G01N 21/4795* (2013.01); *A61B 5/7257* (2013.01); *G01N 2021/1787* (2013.01)

SYSTEM AND METHOD FOR CALIBRATED SPECTRAL DOMAIN OPTICAL COHERENCE TOMOGRAPHY AND LOW COHERENCE INTERFEROMETRY

CROSS-REFERENCE TO RELATED APPLICATIONS

This application represents the national stage entry of PCT International Application No. PCT/US2010/058548 filed Dec. 1, 2010, which claims the benefit of U.S. Provisional Patent Application Ser. No. 61/265,571, filed on Dec. 1, 2009, and entitled "SYSTEM AND METHOD FOR ENHANCED SPECTRAL DOMAIN OPTICAL COHERENCE TOMOGRAPHY AND LOW COHERENCE INTERFEROMETRY", both of which are hereby incorporated herein by reference for all purposes.

STATEMENT REGARDING FEDERALLY SPONSORED RESEARCH

This invention was made with United States Government support awarded by the following agency: National Institutes of Health NIH AR44812, NIH HL55686, NIH EB02638/HL63953, NIH AR46996, and NIH EB00419. The United States Government has certain rights in this invention.

FIELD OF THE INVENTION

The field of the invention is systems and methods for optical coherence tomography ("OCT") and low coherence interferometry ("LCI"). More particularly, the invention relates to systems and methods for enhanced spectral domain OCT and LCI.

BACKGROUND OF THE INVENTION

Optical coherence tomography ("OCT"), which is based on low coherence interferometry, measures the depth-resolved back-reflections or back-scattering from an object, for example a biological tissue. OCT can provide up to sub-micron-level image resolution, and at or above video-rate image capturing speed. OCT has demonstrated substantial potential as a minimally-invasive medical imaging modality. Early-stage OCT techniques alter the optical path length in the reference arm of an interferometer to introduce an optical group delay and records the interferogram time sequentially, which is commonly referred to as the time domain OCT ("TD-OCT").

Recently, a group of alternative OCT approaches has attracted considerable attention since they have demonstrated extremely high imaging speed without any mechanical movement in the reference arm that drastically alleviates the complexity of scan mechanics used in TD-OCT. This group of approaches can be generally categorized as spectral domain OCT ("SD-OCT") as these techniques all record the spectral interferograms that can be converted to depth-resolved backreflections by Fourier transform. Although spectral interferometry dates back to the original work of Michelson, Fourier transform approaches have only recently been applied to OCT. SD-OCT is generally divided into two general techniques: swept source OCT ("SS-OCT"); and Fourier domain OCT ("FD-OCT"), or spectral radar. The light sources also differ with different OCT operational modes. TD-OCT and FD-OCT use a wideband source, whereas SS-OCT usually utilizes a swept or tunable laser source.

For the calibration of SD-OCT signals, a variety of methods have been explored. Some of the most recognizable methods include using a fixed filter to pick up a specific wavelength as a point reference. This method can dynamically compensate the instability of the starting point of the sweeping but requires high repeatability of the spectrum. Another method includes using a Fabry-Perot ("FP") interferometer or etalon to generate a frequency, f, comb function or a wavenumber, k, comb function. That is, while the laser wavelength is sweeping, the generated frequency or wavenumber comb function is a series of pulses with a fixed interval between adjacent two pulses. Similar to the FP method, a Mach-Zehnder interferometer ("MZI") can be used to generate a frequency comb function, which may also be referred to as a frequency clock. Unlike the FP clock, the MZI clock is a sinusoid type fringe. This means that the crossing points, which are those points where the fringe signal crosses zero or any non-zero DC level, can also be determined, which provides twice the reference points than a FP clock with the same free spectral range ("FSR"). Balanced detection techniques are not easily implemented in the FP method, which leads to more phase errors in the calibration signal, as well as the potential for excess noise.

Many sophisticated swept laser sources provide a non-linear wavenumber-time ("k-t") relationship, which suggests that a digitized OCT signal, while commonly sampled uniformly in time, is non-uniformly distributed in wavenumber space, or k-space. Poor or imprecise calibration could significantly degrade the system performance in terms of the resolution and the ranging accuracy, as well as other parameters. One study reported a hardware-based calibration by clocking the A/D converter with an uneven sampling in time to compensate for the non-linear sweeping operation. This can reduce the time consumption of software calibration, but increases the overall cost as the electronics are more complex, and is not feasible for different operation frequencies of the source. Similarly, a broadband source can be used and the frequencies swept, such as with a movable grating or prism. Other approaches may employ a wideband source with a tunable filter that scans or selects individual wavelengths. However, the power of any selected wavelength component is always much lower than the total power, which is a drawback of this approach. Moreover, a complex tuning/scanning mechanism is required for precise and repeatable functioning. To overcome the low-power limitation with previous approaches, the more common approach is to use a wideband source that is placed in an external cavity tunable laser as a gain medium, and in which a grating or prism is used as a tuning mechanism. Even in this more common approach, however, the issue of a complex tuning mechanism is present as a drawback.

A nearest neighbor check algorithm is popularly used in current SS-OCT systems for calibration. Its basic concept is using a sliding window with fixed width (e.g., 3 points or 5 points) to select consecutive subsets in the digitized clock data set, then searching for extrema in this subset as a final finding. This algorithm needs less computation and is presumably fast for calculation. However, its accuracy is substantially compromised as it is intrinsically sensitive to noise or phase errors in the calibration signal. Practically, prominent noise cannot be completely eliminated in the calibration signal, which may substantially affect the calibration accuracy. In addition, advanced calibration typically results in an increased processing burden.

Analog-to-digital ("A/D") conversion is a signal-to-noise ratio performance limiting step in current systems employed for both SS-OCT and FD-OCT. The basic component to all A/D conversion is the quantizer, whose output is always the closest discrete level to the analog input. The interval between the discrete levels is usually uniform, which determines the quantization noise. Thus, the maximum SNR of a given A/D converter is limited by the total of these discrete reference levels. Any input signal with a higher SNR than that of the converter will inevitably suffer a signal loss in the stage of A/D conversion. The detection parameters of SS-OCT and FD-OCT appear to be inferior to TD-OCT, contrary to many current opinions. This concern may not be a practical issue for OCT imaging in transparent materials such as human eyes or certain plastics, which have low dynamic range. However, the concern could limit the capability of these techniques to penetrate many non-transparent materials, semi-transparent materials, non-biological materials, or layered or thick samples thereof without improved performance characteristics, including a larger dynamic range and improved SNR.

In light of the foregoing, it would therefore be desirable to provide a more effective SS-OCT calibration system and method that compensate for nonlinearities resulting from vector space conversion and non-repeatability and instability in source sweeping. In doing so, it would be desirable to provide such a method that is more accurate and reliable than those previously existing methods. It would also be desirable to provide a system and method for spectral domain OCT that exhibits a larger dynamic range and improved SNR.

SUMMARY OF THE INVENTION

The present invention overcomes the aforementioned drawbacks by providing a system and method for performing real-time calibration of signal information acquired by spectral domain optical coherence tomography ("OCT"). In addition. A search algorithm for cross-points, peak points, and trough points in the calibration signal is provided by, for example, a genetic algorithm ("GA"). Using the calibration signal and the estimated extrema, a series of more accurate, or "calibration," extrema are subsequently calculated by an interpolation method, such as a cubic spline interpolation. Similarly, using the calibration signal and the estimated crossing points, a series of more accurate, or "calibration," crossing points are calculated using a curve fitting method, such as a linear interpolation. The acquired image or A-scan data, which is conventionally in the form of an interference signal, is then calibrated using these calculated series of calibration extrema or crossing points.

It is an aspect of the invention to provide an optical coherence tomography system that includes a light source, an interferometer in optical communication with a sample and the light source and configured to receive input light therefrom, and a detector in optical communication with the interferometer and configured to receive output light therefrom. The system may also include a logarithmic amplifier in communication with the light source and configured to receive and amplify therefrom a calibration signal. The optical coherence tomography system further includes a processor coupled to the detector, the light source, the processor being configured to receive a signal from the detector; determine, from the received signal, an interference signal indicative of interference patterns in the output light; receive the calibration signal; identify a series of extrema and a series of crossing values in the received calibration signal; identify a series of calibration extrema from the identified series of extrema and received calibration signal by performing a first interpolation; identify a series of calibration crossing values from the identified series of crossing values and received calibration signal by performing a second interpolation; calibrate the interference signal using the using the identified series of calibration extrema and series of calibration crossing values; and reconstruct an image of the sample from the recalibrated interference signal. The system may also include a logarithmic amplifier in communication with the detector for amplifying the interference signal so that its dynamic range is increased.

It is another aspect of the invention to provide an optical coherence tomography system that includes a light source, a detector, and an interferometer in optical communication with the light source and the detector. A logarithmic amplifier is provided to be in communication with the light source and configured to receive and amplify a calibration signal therefrom. A processor is provided to be in communication with the logarithmic amplifier and the interferometer, and the processor is configured to receive a spectral interference signal from the detector; receive the amplified calibration signal from the logarithmic amplifier; calibrate the received spectral interference signal using the received amplified calibration signal; and produce an image having an increased dynamic range from the calibrated spectral interference signal.

It is yet another aspect of the invention to provide a method for producing an image of a subject with an OCT system. At least one of a reference path and a sample path, which is in optical communication with the subject, of the OCT system are illuminated with a light source. An interference signal is then identified from the reference and sample paths of the OCT system, and a calibration signal acquired from light emitted by the light source. The calibration signal may be amplified with a logarithmic amplifier to produce an amplified calibration signal that is more robust to phase errors and to fluctuations in the original calibration signal. A series of extrema and a series of crossing values are then estimated from the acquired calibration signal. From these values and the calibration signal, a first and second series, respectively, of calibration characteristics are identified using, respectively, a first and second interpolation. The interference signal is then calibrated using at least one of the identified first and second series of calibration characteristics and an image of the subject reconstructed using the calibrated interference signal. The interference signal may optionally be logarithmically amplified prior to an analog-to-digital conversion to increase its dynamic range after analog-to-digital conversion.

It is yet another aspect of the invention to provide a method for producing an image of a subject with an optical coherence tomography (OCT) system. At least one of a reference path of the OCT system and a sample path of the OCT system, the latter which is in optical communication with a subject, is illuminated with a light source. An interference signal is identified from the reference and sample paths of the OCT system, and a calibration signal is acquired from light emitted by the light source. At least one characteristic of the calibration signal is identified, and a first series of calibration characteristics is identified from the at least one characteristic of acquired calibration signal by performing a first interpolation. Additionally, a second series of calibration characteristics is identified from the at least one characteristic of acquired calibration signal by performing a second interpolation. The interference signal is then calibrated using the first and second series of calibration characteristics, and an image of the subject reconstructed using the calibrated interference signal.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The theoretical analysis of a spectral-domain ("SD") optical coherence tomography ("OCT") system, such as a swept-source OCT ("SS-OCT") or Fourier domain OCT ("FD-OCT") system, is based, for example, on a free-space Michelson interferometer. This simplification generally holds regardless of the differences in interferogram measurement or whether the system is configured in free space or fiber-optically, and whether a different interferometer is employed. While reference is made herein to OCT systems and methods, it will be appreciated by those skilled in the art that the systems and methods are also applicable for low coherence interferometry.

Figure 1:
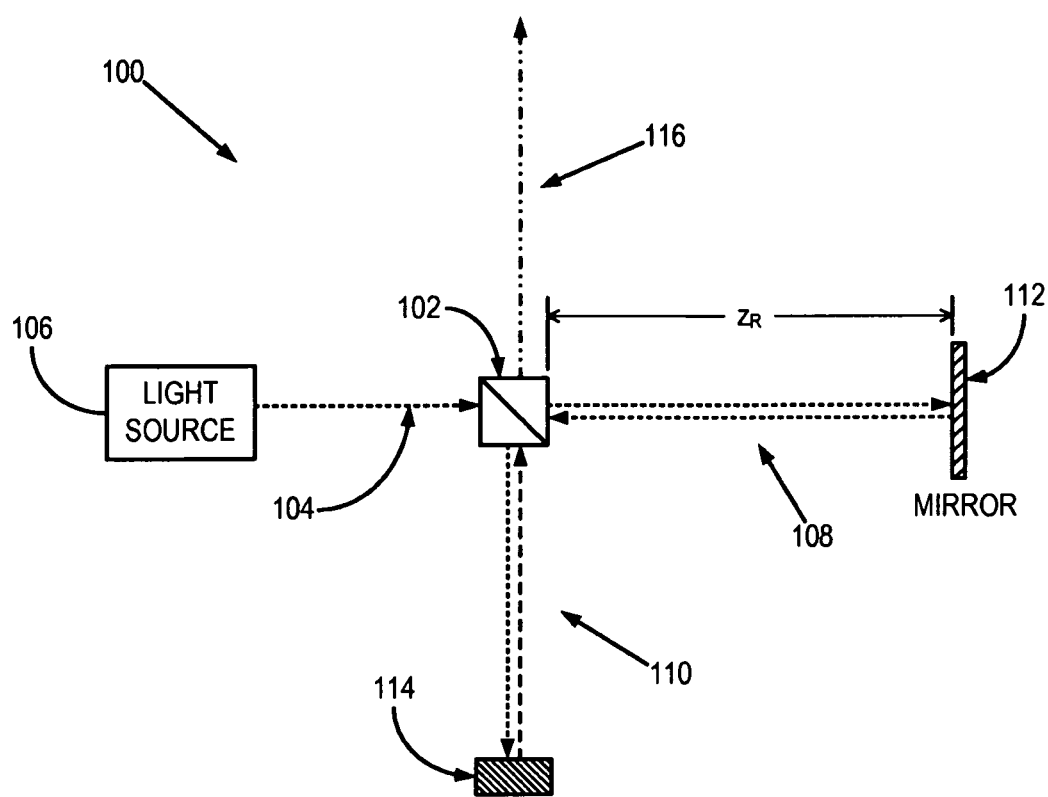
FIG. 1 is a graphic representation of an exemplary free-space Michelson interferometer.

An exemplary configuration of a free-space Michelson interferometer 100 is depicted in FIG. 1, to which reference is now made. A coupler 102 that also acts as a beam splitter, such as a 50:50 beam splitter, divides a light beam 104 from a light source 106 into a reference arm 108 and a sample arm 110 of the interferometer 100. In the reference arm 108, the light beam 104 is returned by a mirror 112 with amplitude reflectivity, $r_R$. The light beam 104 in the sample arm 110 is projected onto a sample 114, usually being focused to provide a desired lateral resolution. Exemplary samples 114 include biological tissues whether in vivo or in vitro. Fresnel reflections occur at any discontinuities of refractive index within the sample 114. These reflected waves carry information about the microstructures of the sample 114, and are collected and returned to the coupler 102. Both returned beams are combined at the coupler 102, thereby generating an interferogram at the exit 116 of the interferometer 100. To further simplify this theoretical analysis, it is assumed that there are no insertion losses, or dispersion or polarization effects in the optical paths; however, it is noted that these assumptions do not detract from the broad applicability of the systems and methods described herein.

The incident light field at the coupler 102 is typically classically described as a complex function whose real part represents the real light disturbance, and is conjugated with the imaginary part through a Hilbert transform as follows:

$$E_0(t) = \int_0^\infty a_0(v) e^{i(\phi_0(v) - 2\pi v t)} dv \tag{1};$$

where $a_0(v)$ and $\phi_0(v)$ represents the real-value amplitude and phase spectrum of the incident light, respectively, and $v$ is the frequency of the light. Thus, the intensity of this light beam is represented by:

$$I_0 = \frac{1}{2}\langle E_0(t) E_0^*(t)\rangle = \int_{-\infty}^\infty S(v) dv = 2\int_0^\infty S(v) dv; \tag{2}$$

where $S(v)$ represents the power spectrum. According to Wiener-Khinchin theorem, the autocorrelation function, $\Gamma_0(t)$, of the incident light beam is the inverse Fourier transform of the power spectrum, $S(v)$:

$$\Gamma_0(t) = \int_{-\infty}^\infty S(v) e^{i2\pi v t} dv \tag{3}.$$

This autocorrelation function is a real real-value function of time, t, considering the symmetry between the positive-frequency part and the negative-frequency part of the power spectrum, $S(v)$. In practice, the measured or generated light spectrum spans the positive frequency range in accordance with the form of $2 \cdot S(v)$.

Referring still to FIG. 1, for SD-OCT techniques, the mirror 112 in the reference arm 108 is generally in a static position for a given interferogram generation. Thus, a spectral interferogram is measured either by placing a spectrometer at the exit 116 of the interferometer 100, or by sweeping out the spectrum, $S(k)$, as a function of wavenumber, k, in time. The former approach is usually referred as Fourier domain OCT, and the latter as swept-source OCT. Accordingly, the individual spectral components of the light field from both the reference arm 108 and the sample arm 110 can be respectively described as:

$$E_R(t, k) = \frac{1}{2} r_R a_0(k) e^{i\phi_0(k)} e^{i2\pi v t} \int_{-\infty}^\infty e^{-i2\pi k z_R} dz; \tag{4}$$

$$E_S(t, k) = \frac{1}{2} a_0(k) e^{i\phi_0(k)} e^{i2\pi v t} \int_{-\infty}^\infty r_S(z) e^{-i2\pi k z} dz; \tag{5}$$

where the phase term in the integral of Eqn. (4) is introduced by the reference mirror 112 being position a distance, $z_R$, away from the coupler 102; the coefficient, $r_R/2$, indicates that the amplitude reflectivity of the mirror 112 is set as $r_R$; and the light beam 104 is split twice by the coupler 102. Similarly, in Eqn. (5), the term $r_S(z)$ represents the backscattering potential of sample 114, and is assumed to be independent of the wavelength, λ. The variable, z, is a distance measured from the coupler 102 to a given backscatter, and the integral over z reflects all the contributions to the returned sample beam from the scattering potential. When the backscatter is a single backscatter event, the distance, z, is an optical distance. The intensity of each spectral component at the exit 116 of the interferometer is:

$$I_D(k) = \frac{1}{2}\langle (E_R(t,k)+E_S(t,k))\cdot(E_R(t,k)+E_S(t,k))^*\rangle \quad (6)$$

$$= \frac{1}{2}\langle E_R(t,k)E_R^*(t,k)\rangle + \frac{1}{2}\langle E_S(t,k)+E_S^*(t,k)\rangle +$$

$$\frac{1}{2}\langle E_R(t,k)E_S^*(t,k)\rangle + \frac{1}{2}\langle E_S(t,k)E_R^*(t,k)\rangle.$$

Accordingly:

$$I_R(k) = \frac{1}{2}\langle E_R(t,k)E_R^*(t,k)\rangle = \frac{1}{4}S(k)r_R^2; \quad (7)$$

$$I_S(k) = \frac{1}{2}\langle E_S(t,k)E_S^*(t,k)\rangle = \frac{1}{4}S(k)\cdot|FT\{r_S(z)\}|^2; \quad (8)$$

and where the remainder of Eqn. (6) can be given by, $$\frac{1}{2}\langle E_R(t,k)E_S^*(t,k)\rangle + \frac{1}{2}\langle E_S(t,k)+E_R^*(t,k)\rangle = \quad (9)$$

$$\frac{1}{4}S(k)r_R \cdot (FT\{r_S(z-z_R)\} + FT\{r_S(z_R-z)\});$$

where FT{. . .} in Eqns. (7)-(9) indicates the Fourier transform operation. Substituting Eqns. (7)-(9) into Eqn. (6), the spectral interferogram at the exit 116 of the interferometer can be described as:

$$I_D(k) = \frac{1}{4}S(k)\cdot\begin{bmatrix} r_R^2 + r_R(FT\{r_S(z-z_R)\}+FT\{r_S(z_R-z)\}) + \\ |FT\{r_S(z)\}|^2 \end{bmatrix} \quad (10)$$

By taking the inverse Fourier transform of the spectral interferogram, $I_D(k)$, presented in Eqn. (10), a real-valued function of the single variable, z, can be obtained:

$$FT^{-1}\{I_D(k)\} = \quad (11)$$

$$\frac{1}{4}FT^{-1}\{S(k)\}\otimes\begin{bmatrix} r_R^2\delta(z) + r_Rr_S(z-z_R) + r_Rr_S(z_R-z) + \\ FT^{-1}\{|FT\{r_S(z)\}|^2\} \end{bmatrix};$$

where "⊗" indicates the convolution operation and δ(z) is the Dirac delta function. Following again from the Wiener-Khinchin theorem, the last term on the right side of Eqn. (11), $FT^{-1}\{|FT\{r_S(z)\}|^2\}$, is essentially and adequately equivalent to the autocorrelation of the backscattering sample potential, $r_S(z)$, which presents mainly around z=0. The inverse Fourier transform of the spectrum is the autocorrelation function, $\Gamma_0(z)$, in z-space, which is convolved with the four terms in the brackets.

If the mirror 112 position, $z_R$, in the reference arm 108 is offset from the sample 114, that is, if the optical path lengths in both arms differ by an appropriate amount, the third and fourth terms in Eqn. (11), $r_Rr_S(z-z_R)$ and $r_Rr_S(z_R-z)$, respectively, can be distinguished from the other terms, such as the delta function, δ(z), at z=0, and the autocorrelation term of the symmetric backscattering potential around z=0. These third and fourth terms, $r_Rr_S(z-z_R)$ and $r_Rr_S(z_R-z)$, respectively, relate to the scattering potential, and are designated to be retrieved.

On the other hand, manipulation of the optical path length in the sample arm 110, z, can also be utilized to distinguish the two scattering potential terms in Eqn. (11) separate from each other because they are symmetrical with respect to $z=z_R$, thereby allowing isolation of these terms. It is useful to notice that, practically, the sweeping or measurement of the spectrum obtains only the positive wavenumber part of the spectral interferogram in Eqn. (10), in the appropriate device configuration, which means the inverse Fourier transform in Eqn. (11) will generate a complex function. Thus, the modulus is calculated to retrieve $r_S(z)$.

Practically, in SS-OCT, the spectrum is swept in the time domain, which means the acquired spectral interferogram of the detector is intended to perform linearly in the time domain. Thus, the intensity, $I_D(t)$, is a function of time instead of the wavenumber. Because of this, the intensity, $I_D(t)$, must be transformed into wavenumber space, or k-space, before performing the inverse Fourier transform in Eqn. (11). Therefore, the relationships between the wavenumber, k, and the sweeping time, t, in terms of a function k=f(t) must be taken into account. Using the wavenumber-time relationship, the interferogram in k-space can be obtained as $I_D(f^{-1}(k))$. This process is generally referred as "calibration" in SD-OCT.

Given a strict linear relationship between k and t, as follows:

$$k = \frac{\Delta k}{\Delta t}t + k_0; \quad (12)$$

where Δt is the sampling window in the time domain; Δk is the wavenumber range in the time interval Δt; Δk/Δt represents the constant sweeping speed; $k_0$ is the center wavenumber; and t ranges from −Δt/2 to Δt/2, the transformed k-space interferogram is given by:

$$I_D(k) = \frac{1}{4}S\left(\frac{\Delta T}{\Delta k}(k-k_0)\right)\cdot\begin{bmatrix} r_R^2 + \\ r_R(FT\{r_Sz-z_R\}+FT\{r_S(z_R-z)\}) + \\ |FT\{r_S(z)\}|^2 \end{bmatrix}. \quad (13)$$

The inverse Fourier transform on this converted interferogram, thus, becomes:

$$FT^{-1}\{I_D(k)\} \propto \Gamma_0\left(\frac{\Delta k}{\Delta T}z\right)\otimes\begin{bmatrix} r_R^2\delta\left(\frac{\Delta k}{\Delta T}z\right) + \\ r_Rr_S\frac{\Delta k}{\Delta T}(z-z_R) + \\ r_Rr_S\frac{\Delta k}{\Delta T}(z_R-z) + \\ FT^{-1}\left\{\left|FT\left\{r_S\left(\frac{\Delta k}{\Delta T}z\right)\right\}\right|^2\right\} \end{bmatrix}; \quad (14)$$

which indicates that, for such a linear relationship as the one in Eqn. (12), the inverse Fourier transform can be directly applied on $I_D(t)$. Consequently, the designated profile can then be retrieved by rescaling the data in the z-dimension. However, many kinds of sophisticated swept laser sources can provide relationships that approach linearity, to some degree, between the wavelength, $\lambda$, and time, t, such as:

$$\lambda = \frac{\Delta\lambda}{\Delta T}t + \lambda_0; \quad (15)$$

where $\Delta\lambda/\Delta t$ represents the constant wavelength sweeping speed; $\lambda_0$ is the central wavelength; and t ranges from $-\Delta t/2$ to $\Delta t/2$. This linearity in wavelength, $\lambda$, indicates a nonlinearity between k and t because:

$$t = \frac{\Delta T}{\Delta\lambda}(\lambda - \lambda_0) = \frac{\Delta T}{\Delta\lambda}\left(\frac{1}{k} - \frac{1}{k_0}\right). \quad (16)$$

Expanding the term in the parenthesis into its power series around $k_0$, Eqn. (16) becomes:

$$t = \frac{\Delta T}{\Delta\lambda}\left[-\frac{1}{k_0}\left(\frac{k}{k_0} - 1\right) + \frac{1}{k_0}\left(\frac{k}{k_0} - 1\right)^2 + \frac{1}{k_0}\left(\frac{k}{k_0} - 1\right)^3 + \ldots\right]. \quad (17)$$

Eqn. (17) indicates that this nonlinearity, which is frequently referred to as an issue of non-uniform sampling, will introduce a series of nonlinear terms in the converted spectral interferogram in k-space. These nonlinearities cause distortions in the autocorrelation $\Gamma_0(z)$, and diminish the spatial resolution and ranging accuracy of the SS-OCT system. If a priori knowledge of the nonlinearities exists and is employed, the calibration becomes necessary to perform only before each OCT operation. Unfortunately, such a priori information is not commonly known for many laser sweeping mechanisms, particularly with respect to the stability and repeatability of the spectrum sweeping. For example, a common mechanism of irregularities in SS-OCT results from using a lead zirconate titanate ("PZT") resonator in the tuning mechanism. The hysteresis of the PZT affects the repeatability and linearity of the spectrum. In addition, stability errors can be caused a variety of sources, such as jitter noise in the PZT resonator driving signals. Thus, a real-time calibration is highly desirable and demanded.

In an exemplary SS-OCT system employed when practicing the present invention, a Mach-Zehnder interferometer ("MZI") is used for the real-time calibration and compensation purposes. It will be appreciated by those skilled in the art, however, that other interferometers may also be used to produce a calibration signal as described herein. An MZI is one configuration of a two-beam interferometer. The intensity of the MZI output periodically changes if the wavelength of the monochromatic or quasi-monochromatic light source at the input is scanning. This output signal contains maxima and minima that are equally spaced in the optical frequency domain, or equivalently, the wavenumber domain ("k-space"). The difference between two maxima is defined by the free spectral range ("FSR") of the interferometer, which is determined by the optical-path-length-mismatch between both arms in the MZI. An exemplary FSR is set at around 100 GHz, which corresponds to a wavenumber interval of around 3.33 per centimeters ("cm$^{-1}$"). Zero-crossings in the electronic output signal of the MZI are also used, as described below. In an SS-OCT system, the wavelength of the laser source is rapidly tuned. As the extrema and crossing-points are determined in a temporal sequence, they are used to index the dataset of the simultaneously captured spectral interferogram. Thus, the OCT signal is transformed into a set of data with a fixed wavenumber interval before fast Fourier transform processing.

Figure 2:
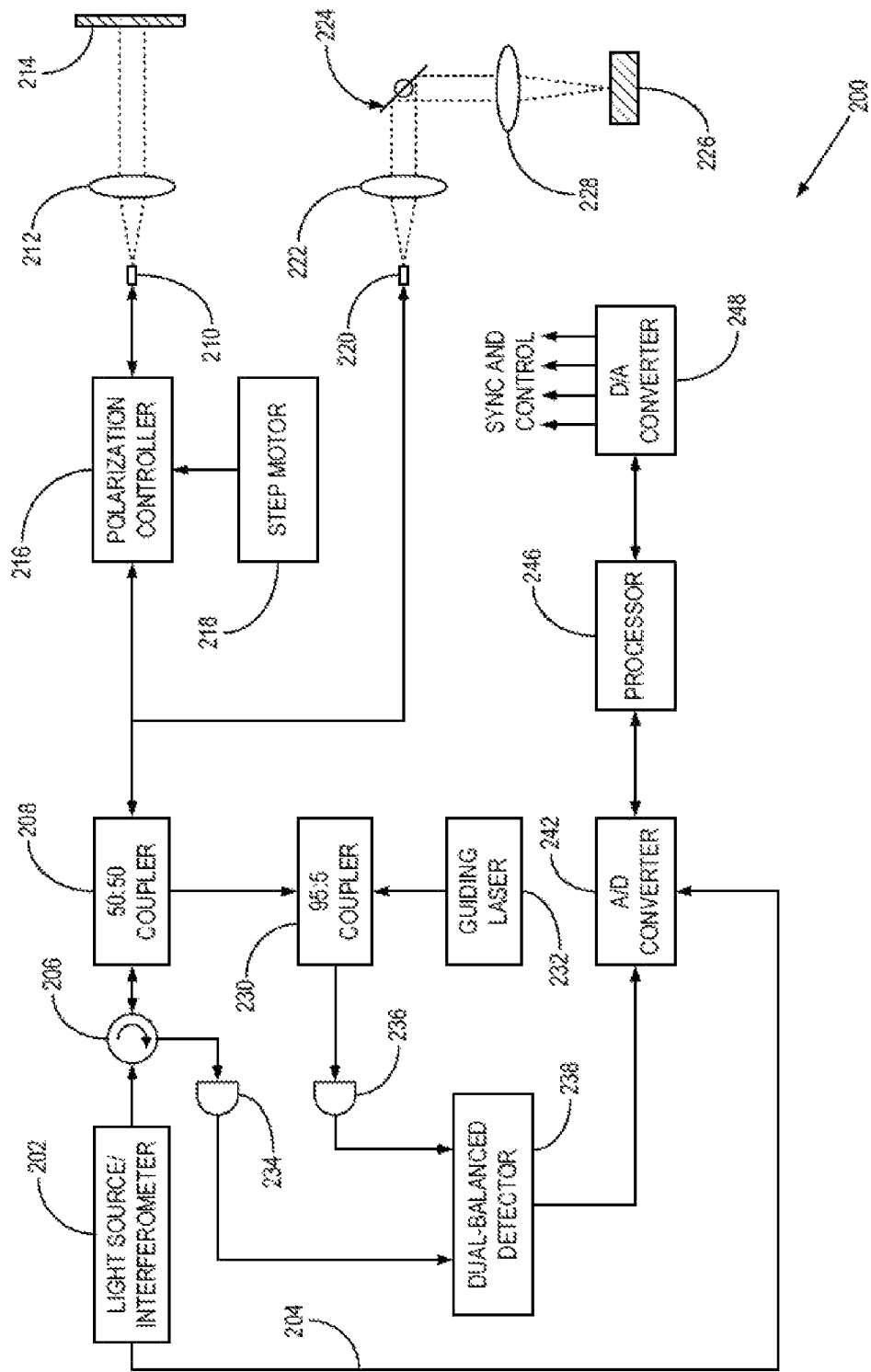
FIG. 2 is a block diagram of an exemplary swept-source optical coherence tomography ("SS-OCT") system employed when practicing some embodiments of the present invention.

The general optical arrangement of an exemplary high speed SS-OCT system 200 is depicted in FIG. 2. Such an exemplary SS-OCT system 200 includes a fiber optic Michelson interferometer as a central component of the system architecture. It will be readily appreciated by those skilled in the art, however, that the succeeding discussion is directed to only one of many different possible configurations of such an SS-OCT system. A light source 202, such as a swept laser source, provides, for example, 100 nanometer ("nm") full-width half-maximum ("FWHM") wavelength scan range at, for example, a central wavelength of 1325 nm, as well as 10 mW output power. Those skilled in the art will appreciate that light source parameters, such as the central wavelength, can be changed depending on the particular application at hand, the particular imaging needs, or given availability. The wavelength sweeping rate is, for example, 16 kHz, and the instantaneous coherence length of the laser is measured to be, for example, greater than 7 mm.

In such a light source 202, a Mach-Zehnder interferometer is embedded to provide a frequency clock with, for example, 100 GHz optical frequency space (around 0.6 nm in wavelength). An analog calibration signal is outputted from the MZI in the light source 202 along line 204. This calibration signal is utilized for real-time spectrum calibration in the SS-OCT system 200.

The light beam produced by the light source 202 is guided into a circulator 206 and an optical fiber coupler 208, such as a 2×2 50:50 fiber coupler. The two output ports of the optical fiber coupler 208 compose the two arms of the Michelson interferometer. One arm referred to as the reference arm, is projected by a fiber collimator 210 through a lens 212 into a mirror 214, which is movable along the beam direction through a micro-stage. In an exemplary configuration of the reference arm, a motorized Lefevre type polarization controller 216 may be built and implemented for polarization measurement or control with the SS-OCT system 200. The polarization controller 216 may be controlled by a step motor 218 to change the polarization of the light beam in the reference arm. For a Lefevre polarization controller, the step motor 218 changes, for example, the diameters of the optical fiber loops in the polarization controller 216, thereby changing the polarization of the light transmitted through the polarization controller 216. It will be appreciated by those skilled in the art that polarization controllers other than Lefevre type controllers can also be implemented. For example, the polarization may be controlled by way of the addition and removal of wave plates, such as quarter-wave plates or half-wave plates, in the reference arm. Additionally, fiber-based polarization controllers other than Lefevre polarization controllers can be implemented, such as those that operate by compressing an optical fiber to induce a variable birefringence in the optical fiber. It will also be appreciated by those skilled in the art that the intensity of the light beam in the reference arm may also be changed by the polarization controller 216 by way of changing the polarization of the light beam in the reference arm.

The second arm, referred to as the sample arm, is projected by a fiber collimator 220 through a lens 222 onto an X-Y scanner 224. The scanned beam is then focused on a sample 226 through an objective lens 228 having, for example, a 30 mm focal length. The X-Y scanner 224 is synchronized with the light source sweeping so that so-called B-scanning and third-dimension scanning is provided for OCT imaging. Three-dimensional imaging is provided, for example, by adding multiple B-scans together.

The light beams returning from the reference and sample arms combine and interfere at the optical fiber coupler 208, thereby producing interferograms. These interferograms are provided from two ports of the optical fiber coupler 208 and guided into a the circulator 206 and a second coupler 230. This second coupler 230 has, for example, 95:5 splitting ratio and also helps to guide a beam from a guiding laser 232 to both the reference and sample arms. The interferograms from the circulator 206 and second coupler 230 are provided to detectors 234, 236 before passing to a dual-balanced detector 238.

The digital spectral interference and calibration signals are provided from the A/D converter 242 to a processor 246 for calibration, image generation, and other processing tasks. The processor 246 may include, for example, capabilities for parallel and synchronous acquisition of two channels for recording the spectral interference signal from the dual-balanced detector and the calibration signal from the MZI by controlling and communication with the A/D converter 242. The control signal for the X-Y scanner and the system synchronization are generated through a digital-to-analog ("D/A") converter 248, and are subsequently supplied to the appropriate components of the SS-OCT system 200.

Figure 3:
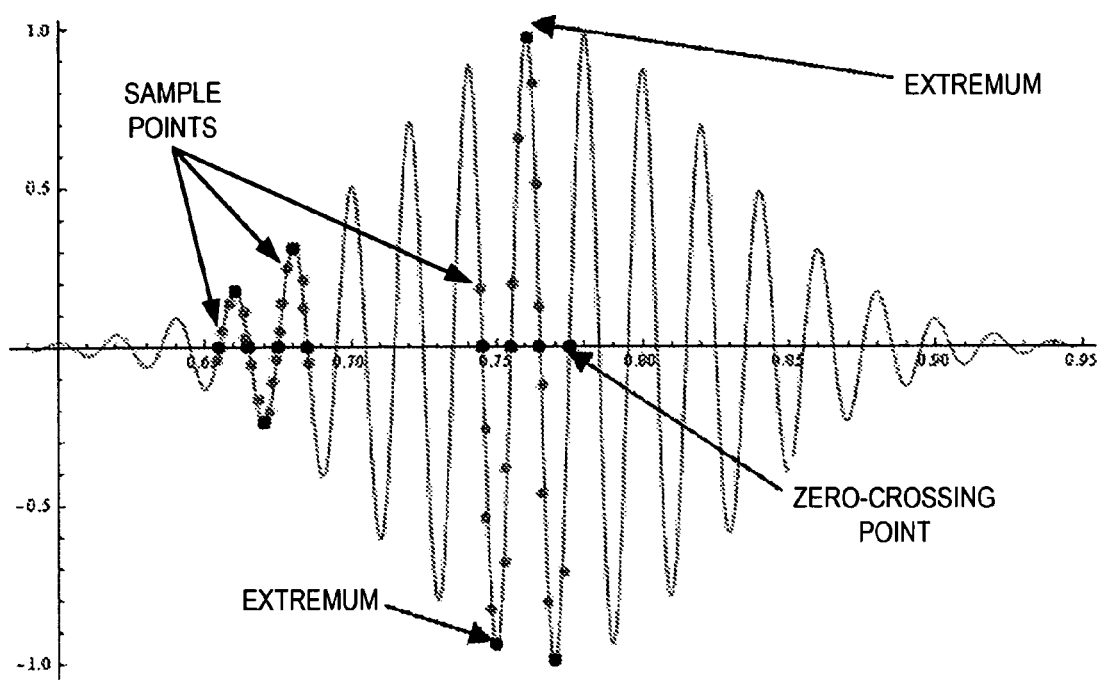
FIG. 3 is a graphic representation of an exemplary calibration signal, or frequency clock signal, produced by a Mach-Zehnder interferometer.

The calibration signal from the MZI is substantially evenly sampled by the A/D converter 242 simultaneously along with the spectral interference signal from the dual-balanced detector 238. However, in other configurations that calibration signal from the MZI can be provided directly to and sampled at the processor 246, thereby bypassing the A/D converter 242. An exemplary calibration signal is illustrated in FIG. 3. As described earlier, the calibration signal is used as a reference with its cycles being substantially equidistant in frequency. The difference between two maxima is defined by the FSR of the MZI.

In one previous study, recalibration was performed using a fast nearest neighbor check algorithm, which is referred as the regular calibration here. A fast search algorithm for peak points and trough points in the calibration signal was performed. If the samples had satisfied the conditions of the algorithm, the corresponding points in the OCT signal were added to the recalibrated signal array. While this method provides speed that is adequate for real-time preview, it fails to determine the actual peaks and troughs and leads to errors or incomplete corrections.

In some embodiments, a genetic algorithm ("GA") is employed to optimize the search method in the calibration trace. An appropriate fitness function is defined in a way that local extremes and vicinity to zero increase the fitness value for extremes (peaks and troughs) and cross points, respectively. The value of the Gaussian envelope of the calibration signal in proximity of each extreme is used as an auxiliary tool for the fitness function. Using this dataset as the first generation, during each successive generation, a number of points are selected based on their quality measured by fitness function. Consecutive iterations of this method increase the average fitness of the population of the next generation. It is noted that multiple generations are achieved in microseconds. This generational process continues, until the requisite number of points with desired quality is attained. At this point the algorithm is terminated. These points are, afterwards, used for interpolation.

In order to find the actual extremes and cross points, two interpolations are performed on the obtained data; however, it should be appreciated by those skilled in the art that more than two interpolations could also be performed, or, alternatively, at least one interpolation and at least one curve fitting method can also be employed. Cubic spline interpolation is performed for the extremes and interference signal, while linear interpolation is done for the cross-points. The functions used here for extremes and interference signal must behave smoothly to avoid the jitter noise. To satisfy this condition, the functions must be differentiable and their second derivative must be continuous. Considering this fact and also to minimize the interpolation error and avoid Runge's phenomenon, spline functions are used here that normally satisfy these requirements. In this example, it should be noted that the samples are acquired at a rate that guarantees that there is substantially only one extremum in each interpolation. However, with more complex approaches, more than one extremum may occur in each interpolation.

Real-time display requires a fast recalibration algorithm. Using multi-threading technique, inverse Fourier transform, GA, and interpolation are performed in parallel for the axial scans, and therefore they do not increase the overall time of the process. This method increases the performance of the system in different ways. First, adding cross points to the reference points leads to doubled sampling frequency and higher accuracy in signal reconstruction. Second, the GA based optimized search and precise interpolation minimizes the errors in finding the reference points, both by reducing nonlinearities from the source and the A/D conversion process during t-to-k space conversion. Image resolution, dynamic range, and image quality are improved by using the proposed method in a SS-OCT system.

Figure 4:
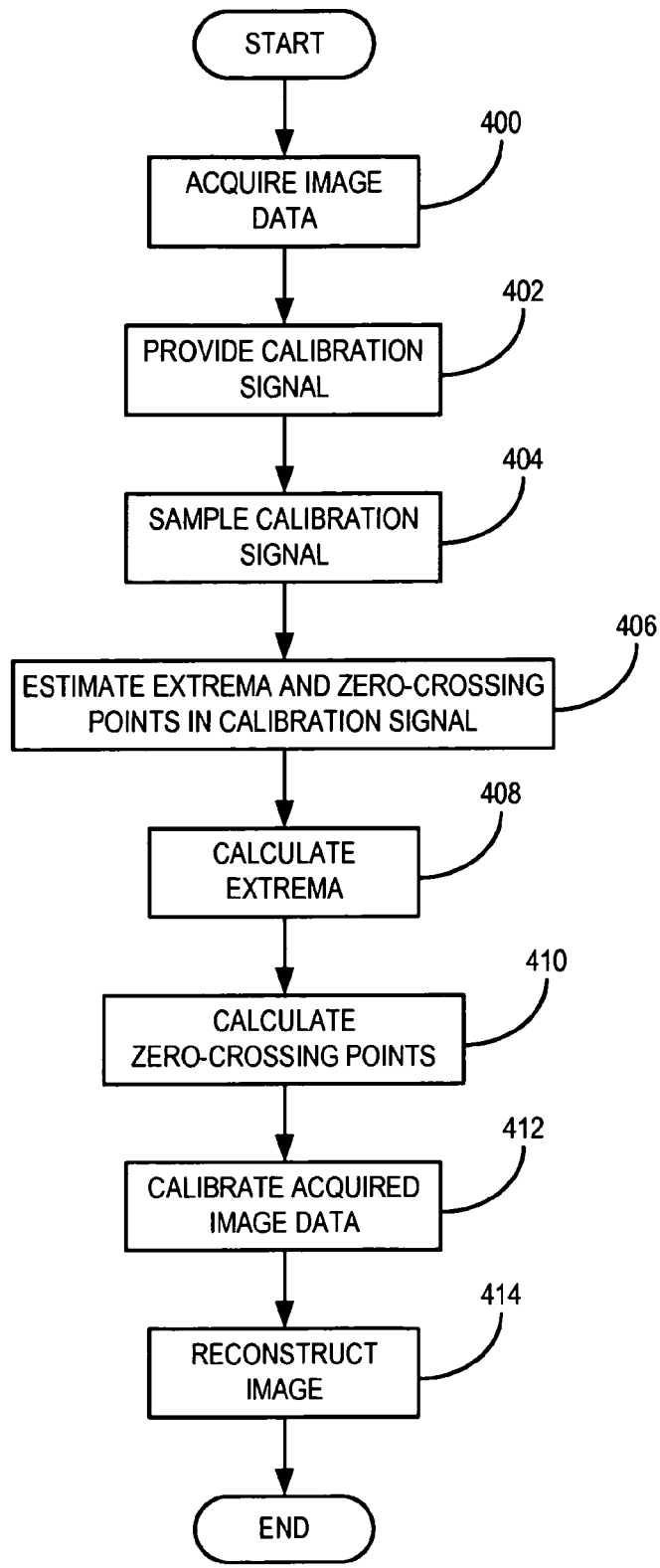
FIG. 4 is a flowchart setting for the steps of an exemplary method for calibration and image reconstruction employed by the OCT system of FIG. 2.

Referring now to FIG. 4, the steps of an exemplary method for reconstructing an image from a calibrated spectral interference signal acquired with, for example, the SS-OCT system of FIG. 2 are illustrated. First, image data is acquired in the form of interference patterns from the reference and sample paths of the OCT system, as indicated at step 400. A calibration signal is similarly provided, as indicated at step 402. For example, and MZI is coupled to the light source of the OCT system, and as a wavelength of the light produced therefrom is swept over a range of values, a calibration signal is produced by the MZI substantially contemporaneous with the acquisition of the image data.

The calibration signal is sampled by an A/D converter to produce a digital representation of the calibration signal that is utilized for processing, as indicated at step 404. In alternative configurations, however, the calibration signal may be sampled directly at the processor. From the digitized calibration signal, estimates of the extrema and crossing points in the calibration signal are produced, as indicated at step 406. These crossing points may be zero-crossing points, DC-crossing points, or other crossing points. As discussed above, the estimation process is performed by searching for the extrema and crossing points with a global optimization method, such as a genetic algorithm ("GA").

Using the calibration signal and the estimated extrema, more accurate extrema are calculated next, as indicated at step 408. This is achieved, for example, by performing a cubic spline interpolation. Likewise, more accurate crossing points are calculated at step 410 using the calibration signal and estimated crossing points. This is achieved, for example, by performing a linear interpolation. The calculated extrema and crossing points are distributed substantially uniformly across an abscissa that represents, for example, either wavelength or wavenumber. These points and their substantially uniform distribution are subsequently utilized to calibrate the acquired image data, as indicated at step 412.

Since the calibration signal was originally produced substantially contemporaneously with the acquisition of the image data, the calibration is achieved by forming a so-called calibrated signal array. Such a calibrated signal array is formed by selecting those values in the acquired image data that are associated with the wavelength or wavenumber values corresponding to the calculated extrema and crossing points. In this manner, the image data is calibrated such that there is a substantially linear relationship between either the wavelength or wavenumber of the acquired image data and the progression of time during which the data was acquired. Using this calibrated signal array, an image of the subject is reconstructed as indicated at step 414.

Figure 5:
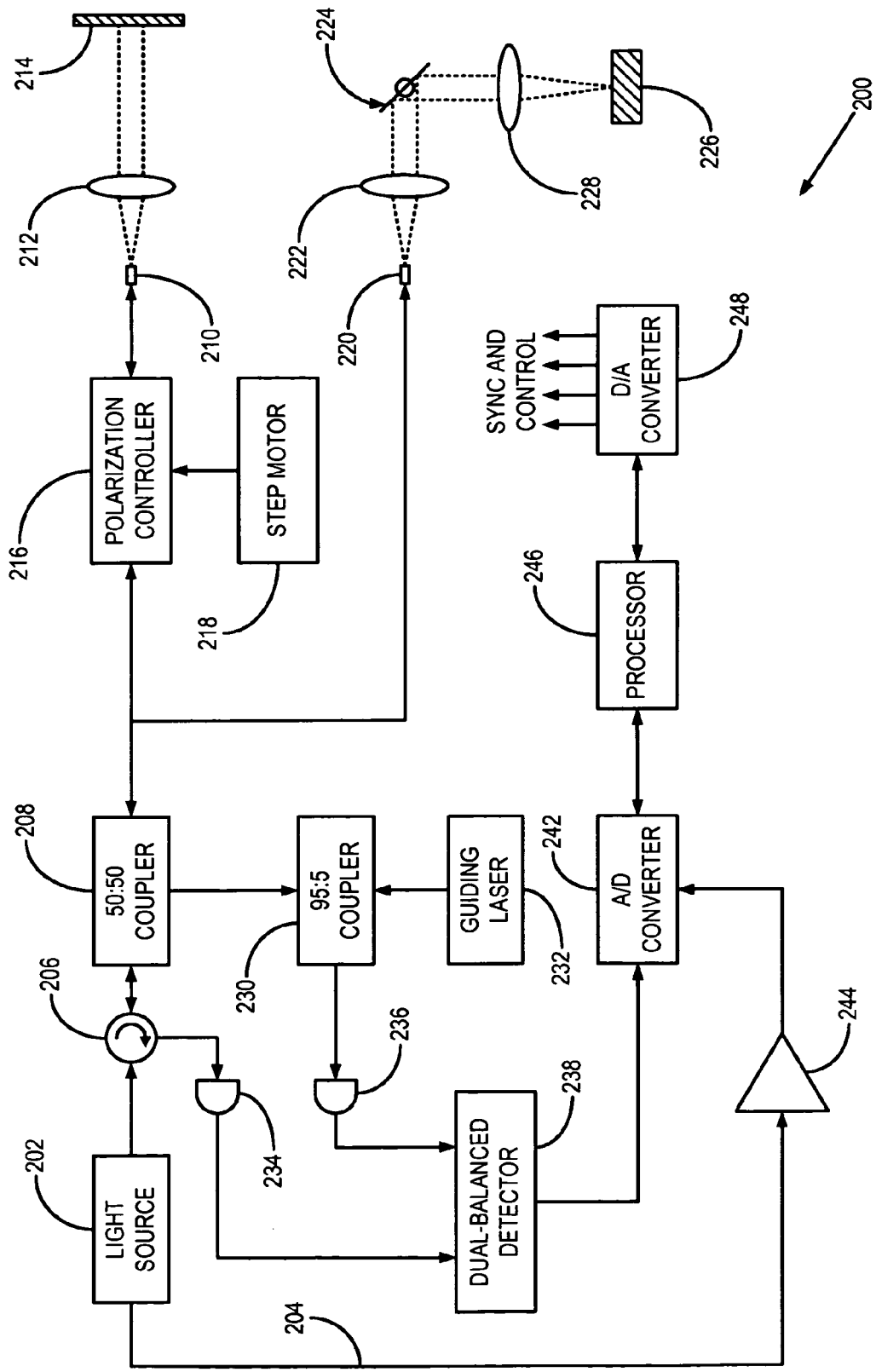
FIG. 5 is a block diagram of an exemplary SS-OCT system that provides a logarithmic amplification of a calibration signal for improved calibration performance.

In some configurations of an SS-OCT system, such as the one illustrated in FIG. 5, the calibration signal on line 204 is additionally amplified by a true logarithmic amplifier 244. Subsequently, this amplified calibration signal is supplied to the A/D converter 240. The amplification of the calibration signal results in a significant improvement in the calibration of the spectral interference signal by improving the searching accuracy for extrema and crossing-points in the calibration signal. The reason for this improvement is two fold. First, a logarithmically-amplified calibration signal is less sensitive to phase errors than a regular calibration signal, and, second, the signal-to-noise ratio ("SNR") of the true logarithmic amplifier 244 output is higher than its input when the input SNR is at or above one. Thus, the logarithmically-amplified calibration signal will have less fluctuation at extreme regions, thereby significantly improving λ-space to k-space calibration accuracy, as well as the accuracy of those calibration techniques where other vector space conversions are used. The logarithmic amplification of the calibration signal also compensates for nonlinearities of the source sweep.

Figure 6:
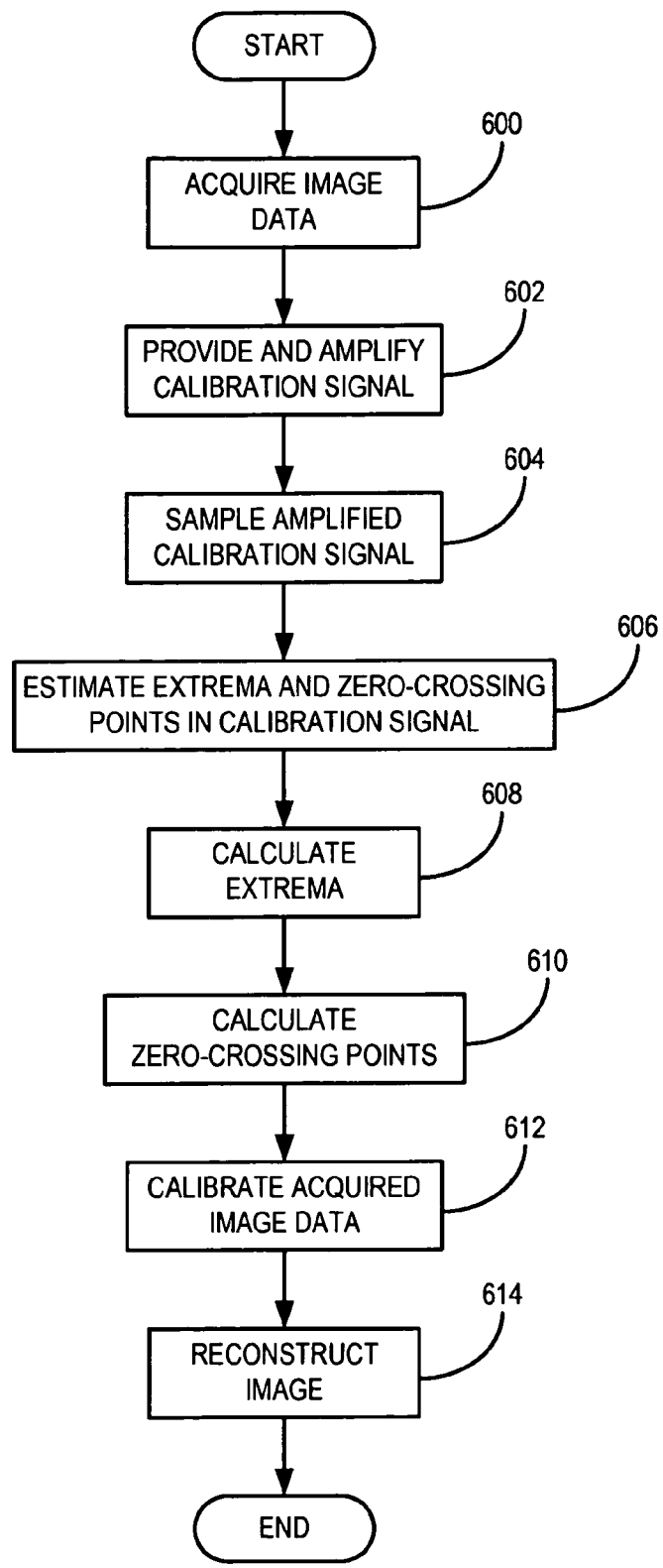
FIG. 6 is a flowchart setting for the steps of an exemplary method for calibration and image reconstruction employed by the OCT system of FIG. 5.

Referring now to FIG. 6, the steps of an exemplary method for reconstructing an image from a calibrated spectral interference signal acquired with, for example, the SS-OCT system of FIG. 5 are illustrated. First, image data is acquired in the form of interference patterns from the reference and sample paths of the OCT system, as indicated at step 600. A calibration signal is similarly provided, as indicated at step 602. For example, an MZI is coupled to the light source of the OCT system, and as a wavelength of the light produced therefrom is swept over a range of values, a calibration signal is produced by the MZI. This calibration signal is produced substantially contemporaneous with the acquisition of the image data. As described above, this calibration signal is amplified by a true logarithmic amplifier so that the extrema and crossing values therein can be more readily identified during the calibration procedure.

After amplification, the calibration signal is sampled by an A/D converter to produce a digital representation of the amplified calibration signal that is utilized for processing, as indicated at step 604. In alternative configurations, the calibration signal may be directly sampled at the processor. From the digitized calibration signal, estimates of the extrema and crossing points in the calibration signal are produced, as indicated at step 606. These crossing points may be zero-crossing points, DC-crossing points, or other crossing points. As discussed above, the estimation process is performed by searching for the extrema and crossing points with a global optimization method, such as a genetic algorithm ("GA").

Using the calibration signal and the estimated extrema, more accurate extrema are calculated next, as indicated at step 608. This is achieved, for example, by performing a cubic spline interpolation. Likewise, more accurate crossing points are calculated at step 610 using the calibration signal and estimated crossing points. This is achieved, for example, by performing a linear interpolation. These points and their substantially uniform distribution are subsequently utilized to calibrate the acquired image data, as indicated at step 612.

Since the calibration signal was originally produced substantially contemporaneously with the acquisition of the image data, the calibration is achieved by forming a so-called calibrated signal data array. Such a calibrated signal data array is formed by selecting those values in the acquired image data that associated with the calculated extrema and crossing points. In this manner, the image data is calibrated such that there is a substantially linear relationship between either the wavelength or wavenumber of the acquired image data and the progression of time during which the data was acquired. Using this calibrated signal array, an image of the subject is reconstructed as indicated at step 614.

By way of example, one definition of the dynamic range of an OCT system is herein defined as the ratio of the maximum detectable reflection signal, $i_{max}$, and the minimum detectable reflection signal, $i_{min}$, after digitization. Dynamic range is a dimensionless parameter that characterizes the intra-A-scan measurement capability of OCT. This capability is important for OCT in the circumstances of imaging tissues and materials that are not transparent, where the reflections from the deep areas of the tissue are substantially lower while other signals, such as the reflections from the surface, can be high enough to saturate in the system. This capability is also important for OCT with respect to separating different intensities for image contrast. By the foregoing definition, the maximum signal, $i_{max}$, could be determined by the maximum detectable reflectivity, $r_{S,max}$, without saturation in the OCT. The minimum signal, $i_{min}$, is usually chosen as same as the sensitivity of the system, which is equivalent to the root-mean-square intensity of the input-referred noise, $\sigma_n$. These noise sources include contributions from both the photon and electron noise sources. The dynamic range can be expressed as:

$$DR = \frac{i_{max}}{i_{min}} = \frac{i_{max}(0)}{\sigma_n} = \frac{r_R r_{S,max} I_0}{2\sigma_n}. \qquad (18)$$

According to the Parseval's theorem and its counterpart for digital signal processing, the energy theorem, the Fourier transform on any signal and noise would not provide any signal to noise ratio improvements. Thus, ideally the dynamic range of either the SS-OCT or the FD-OCT should be identical to the one of TD-OCT. However, this is not true when reducing the theory to practice. By conducting the Fourier transform on a spectral interferogram acquired by TD-OCT and applying Wiener-Khinchin theorem, the dynamic range expression of the SD-OCT will be the same as Eqn. (18) if the equivalent noise source and component limitations in each embodiment are the same. Practically, this principle is not applicable for several reasons. First, as discussed above, TD-OCT is intrinsically a noise-matching filtering system, but SS-OCT and FD-OCT are not. Additional noise sources, such as 1/f and thermal noise in SS-OCT, reduce the dynamic range of SS-OCT as the total noise intensity, $\sigma_n$, increases in Eqn. (18), as discussed below in detail. Second, as shown in FIGS. 4A and 4B, analog-to-digital ("A/D") conversion is a performance limiting step in current embodiments of both SS-OCT and FD-OCT, where logarithmic handling of the signal does not occur prior to the conversion as with TD-OCT. The basic component to all A/D conversion is the quantizer, whose output is always the closest discrete level to the analog input. The interval $\Delta$ between the discrete levels is usually uniform, which determines the quantization noise whose root-mean-square intensity is proportional to $\Delta$. The maximum level of the quantizer is $2^l \Delta$, where l is the bit depth of the ADC. Thus, it is contemplated that the dynamic range of SS-OCT and FD-OCT, as a cascaded system, is inevitably limited by the ADC, which can be expressed as:

$$DR_{ADC-limited} = \frac{r_R r_{S,max} 2^l \Delta}{2\Delta} = r_R r_{S,max} 2^{l-1}. \quad (19)$$

Because $0 \le r_R$ and $r_{S,max} \le 1$, the maximum dynamic range of an ADC-limited OCT system may be as small as $2^{l-1}$. For a 14-bit ADC, this is only about 8096. In FD-OCT, an additional limitation to the dynamic range might arise from the dynamic range of the detector array, which is defined as the ratio of well capacity of the each element and corresponding readout noise. This process is analogous to the digitizer in the ADC, but each discrete level is actually an electron. Thus, according to Eqn. (19), the detector-array-limited dynamic range can be described as:

$$DR_{Array-limited} = \frac{r_R r_{S,max} Q_W}{2\sigma_n}; \quad (20)$$

where $Q_W$ represents the well capacity of individual pixels and $\sigma_n$ represents the prevailing readout noise. For example, if the well capacity of a detector array is 17000 electrons/pixel and the equivalent noise is around 20 electrons/pixel, the dynamic range could be about 8500, which is around the dynamic range limited by the ADC. As a cascaded system, the dynamic range of the FD-OCT will eventually be limited to either ADC or the detector array, depending on which limit arrives first As the limitations of FD-OCT are considerable compared with SS-OCT, most of our efforts here are focused on comparing SS-OCT with TD-OCT.

Figure 7A:
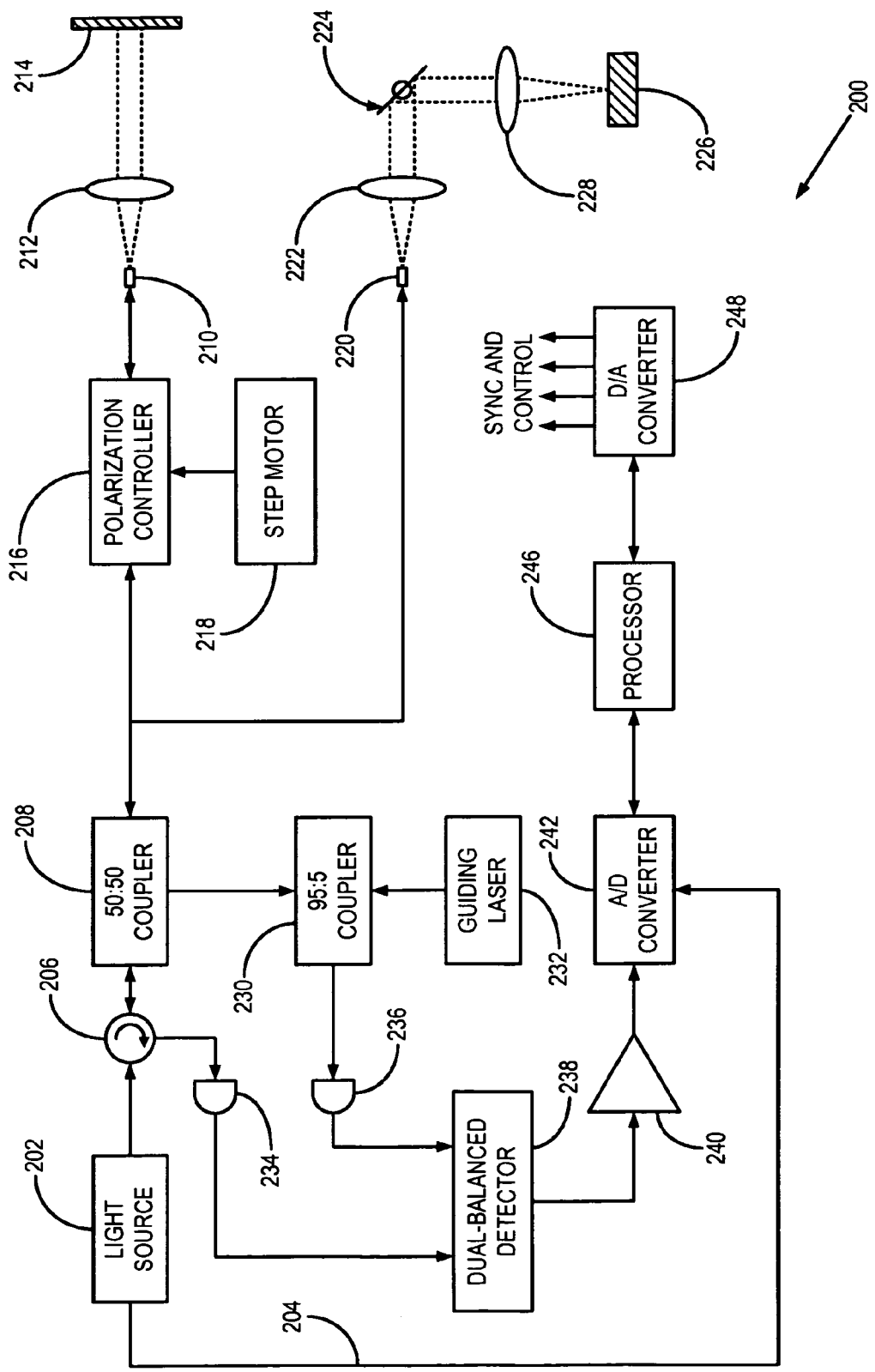
FIG. 7A is a block diagram of an exemplary SS-OCT system that provides a logarithmic amplification of a spectral interference signal for improved dynamic range.
Figure 7B:
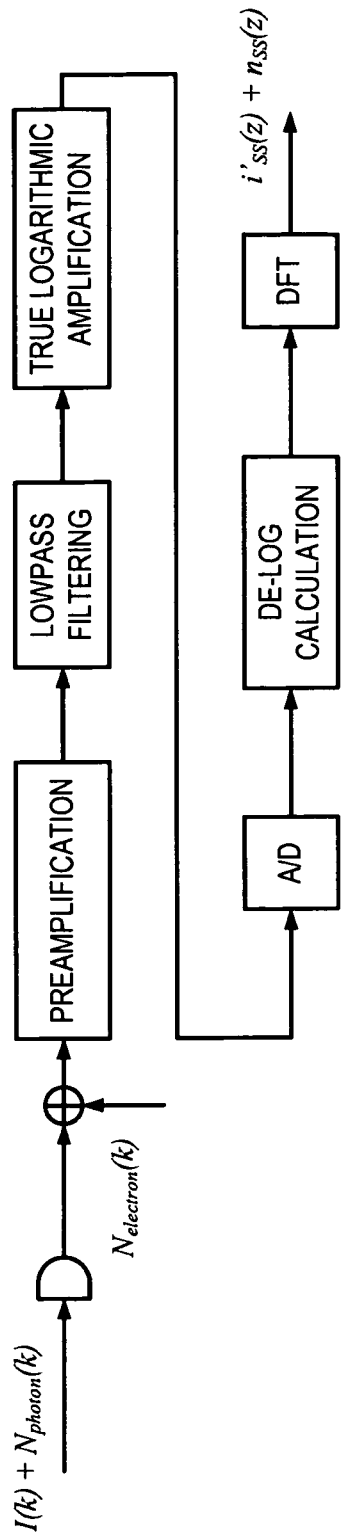
FIG. 7B is a block diagram of the detection system employed in the exemplary SS-OCT system of FIG. 7A.

With TD-OCT, logarithmic amplification is usually utilized before the ADC; thus, the post-digitization dynamic range is approximately 80 dB. With SD-OCT, where a linear signal is applied on the converter, the dynamic range is only 40 dB. This data is in $\log_{10}$ format consistent with original TD-OCT studies. Recently, however, some investigators have used a $\log_{20}$ format terminology to represent dynamic range in decibels without clarification, giving the impression that the performance is doubled. Knowing whether dynamic ranges are presented in $\log_{10}$ or $\log_{20}$ is critical in evaluating data in this filed, as comparing these two different formats is essentially comparing two different units of measurement To overcome the aforementioned drawbacks associated with the SD-OCT, a true logarithmic amplifier ("TLA") is implemented before the ADC in a SS-OCT, as shown in FIGS. 7A and 7B. A true logarithmic amplifier converts the amplitude of signal from linear-scale into log-scale. Based on this nonlinear conversion, the small amplitude components in the signal are magnified and well preserved. Through the TLA, large amplitude components will be compressed. By the logarithmic amplification, signals with wide dynamic range can be well preserved after the A/D conversion, with certain degradations in the resolution of large or small signals depending on how parameters are set. An explicit example is that a signal range from 1-10 volts (9 volts variation) can be converted into 0–1×C counts after the digitization. However, a signal range of 10-100 volts (90 volts change) only varies in the same amount of counts (from 1×C–2×C counts). It is noted that C is a constant representing the amplification. Under certain conditions, such as targets with relatively low dynamic range or focus on surface structures, it may be of use to allow the system to interchange between the logarithmic and linear amplifiers.

Thus, in some configurations of a SS-OCT system, such as those illustrated in FIGS. 7A and 7B, the spectral interference signal from the dual-balanced detector 238 is logarithmically amplified by a true logarithmic amplifier 240, which provides, for example, nominal 90 dB analog signal and a DC 30 MHz operating bandwidth. The use of the true logarithmic amplifier 240 allows a significant extension in the achievable dynamic range in SS-OCT, as described above. The amplified, spectral interference signal is subsequently supplied to the analog-to-digital ("A/D") converter 242. As mentioned earlier, this logarithmic amplification step provides the SS-OCT system 200 with a wider dynamic range than achievable with a conventional SS-OCT system without true logarithmic amplification.

Figure 8:
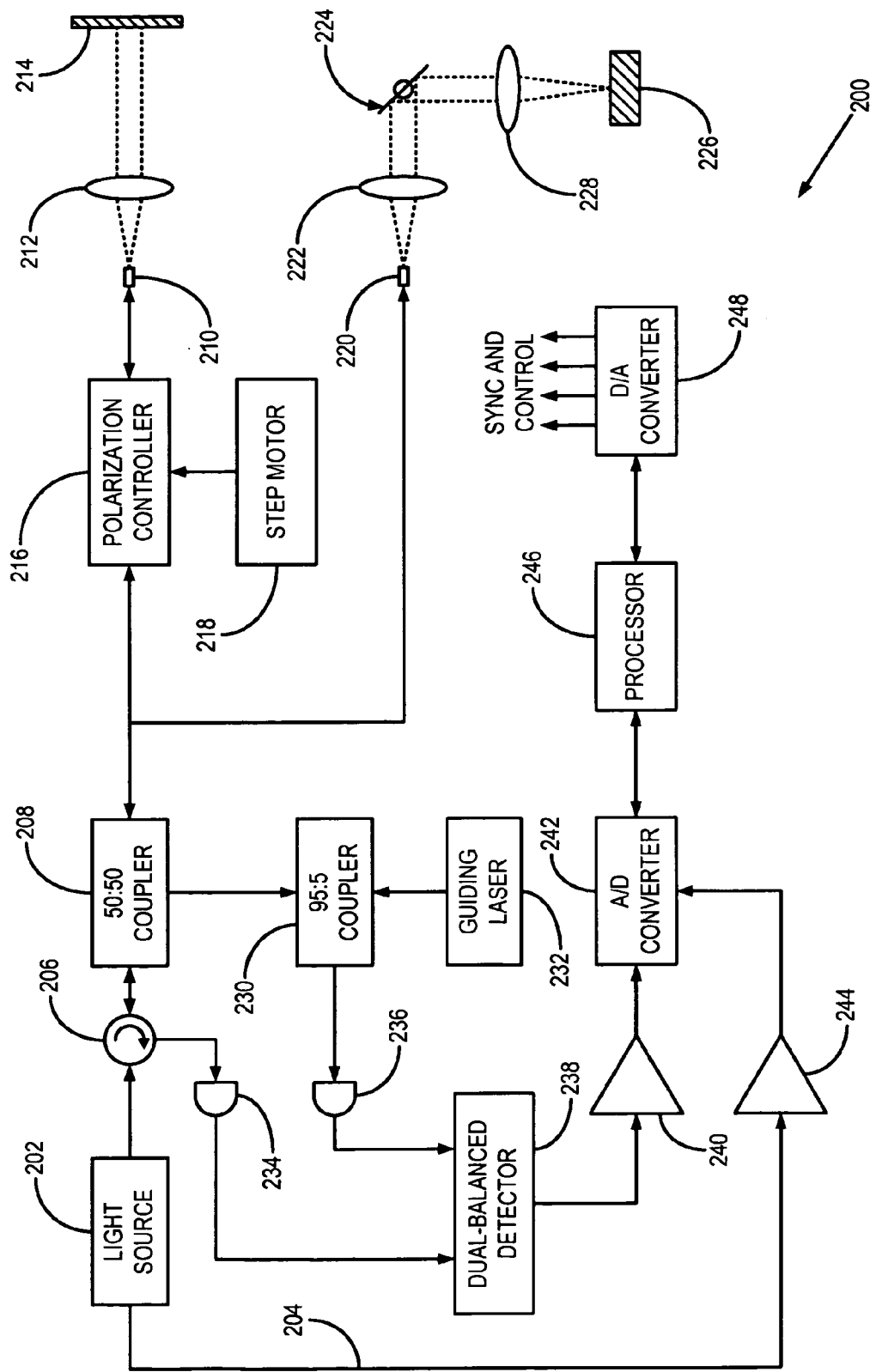
FIG. 8 is a block diagram of an exemplary SS-OCT system that provides a logarithmic amplification of a spectral interference signal for improved dynamic range and of a calibration signal for improved calibration performance.

As illustrated in FIG. 8, in some configurations an SS-OCT system may include a logarithmic amplifier 240 between the dual-balanced detector 238 and the A/D converter 242 for increasing dynamic range in addition to a logarithmic amplifier 244 on the calibration signal line 204 for improving the calibration process, as described above in detail.

Figure 9:
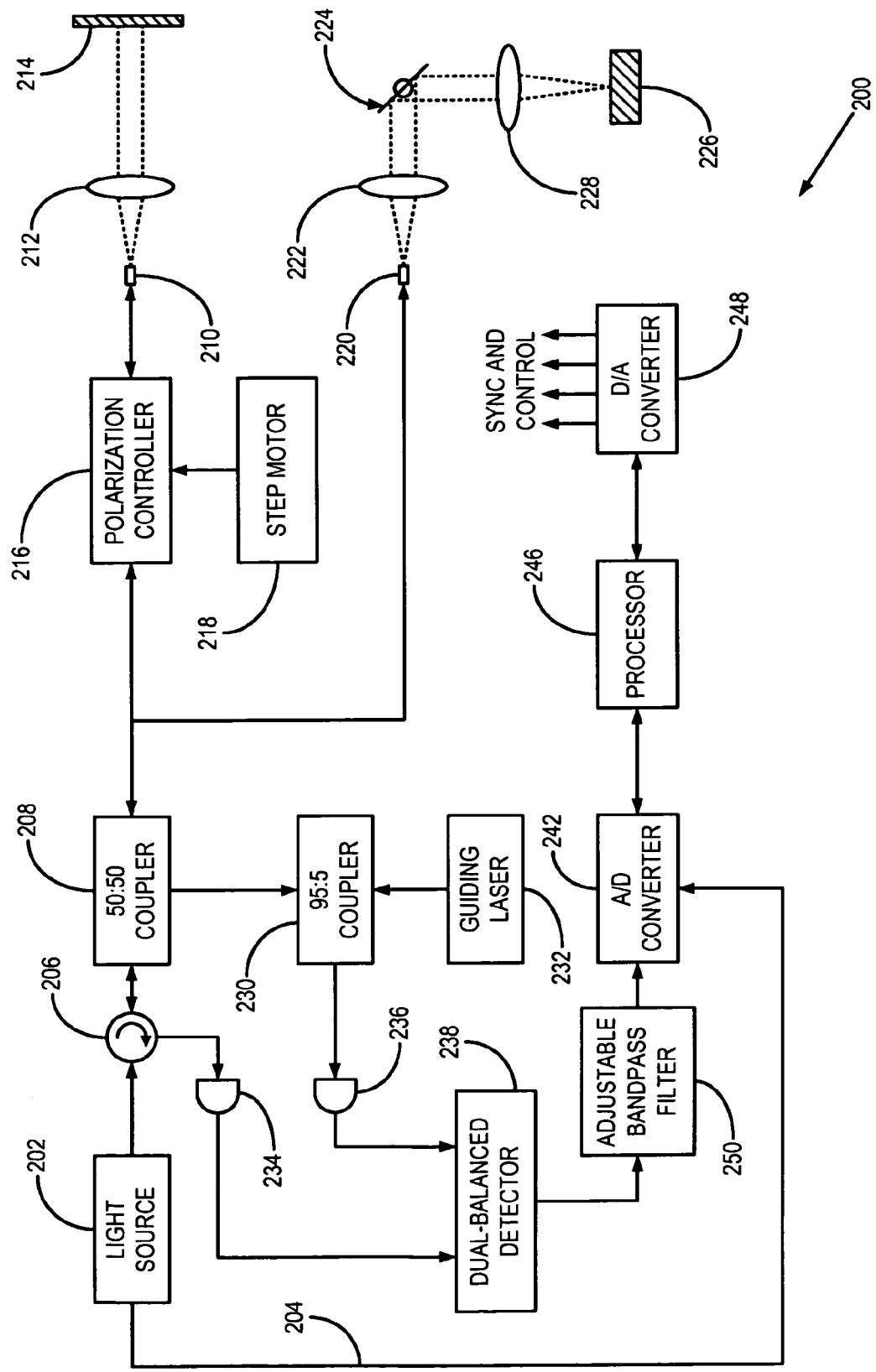
FIG. 9 is a block diagram of an exemplary SS-OCT system that provides an adjustable reference arm mirror in combination with variable band-pass filtering of the spectral interference signal for improved signal-to-noise ratio of the spectral interference signal.

With reference now to FIG. 9, it is desirable that in some configurations of the SS-OCT system, the mirror 214 in the reference arm is configured to be adjustably displaced along an axis perpendicular to the mirror, that is, the "z-axis," is provided. In addition, a variable band-pass filter 250 is provided between the dual-balanced to detector 238 and the A/D converter 242. The variable band-pass filter 250 may include, for example, a single filter whose properties can be altered, or a series of filters that form a filter bank, in which each of the filters in the series of filters has different properties. During operation of the SS-OCT system when the filter bank is used, different filters are selected for their individual properties to vary between different pass bands.

While logarithmic amplifiers on the calibration signal line 204 or between the dual-balanced detector 238 and the A/D converter 242 are not illustrated in FIG. 9, it will be appreciated by those skilled in the art that, as described in detail above, either of these configurations can be combined with the variable band-pass filter 250 configuration described here. When a logarithmic amplifier is also provided between the dual-balanced detector 238 and A/D converter 242, the amplifier may be provided before or after the variable band-pass filter 250. The z-offset provided by the movable mirror 214 is used in connection with the variable band-pass filter 250 in order to effectively shift the autocorrelation function from an area in the subject into a range where substantially all frequencies are detectable, or where unwanted frequencies can be readily removed. In this manner, not only is visualization of the subject enhanced, but factors that deteriorate resolution can be compensated for and complex conjugate ambiguity reduced.

In time domain OCT ("TD-OCT") systems, the mirror scanning in the reference arm acts to moves the spectrum $S(k)$ to a higher frequency, $k_0$, which is ultimately determined by the scanning velocity, V. Thus, a band-pass filter is usually implemented to suppress most of the noise outside the passband, which offers TD-OCT an optimal signal-to-noise performance over the other types of OCT. It is noted that there is typically no Doppler shift or carrier frequencies in SD-OCT techniques. While SS-OCT systems have similar detection electronics as TD-OCT systems in terms of detector and preamplifier, SS-OCT systems are in many respects low-pass filtering systems in which some low frequency noises, such as 1/f noise, including from the detector and amplifier, cannot be easily removed. This indicates that the system is not an optimal system in terms of signal-to-noise performance.

Different from SS-OCT systems, FD-OCT systems introduce additional noise sources because they capture the signal spectrum, $S(k)$, and noise fluctuations, $N(k)$, with a detector array. Usually a contemporary detector array, such as a charge-coupled device ("CCD"), which has an on-focal-plane signal integration function, is used. This signal integration function can be described as a linear summation of the signal spectrum, $S(k)$, and the noise fluctuations, $N(k)$. Because the signal spectrum, $S(k)$, adds coherently, whereas the noise fluctuations, $N(k)$, add incoherently, the signal integration function potentially offers signal-to-noise ratio ("SNR") improvement for FD-OCT. However, like SS-OCT, FD-OCT is also a low-pass filtering system, which is not an optimal detecting system. In addition, it should be noted that noise sources that are only present in the detector array, such as readout and reset noise, compromise the benefits provided by signal integration. Inevitably, this signal integration function likely decreases the dynamic range of the FD-OCT system.

The band-pass filter and z-offset can be varied separately, similar to, for example, the brightness and contrast adjustments on an ultrasound machine. Then the operator, or an electronically controlled image parameters monitor, can make adjustments to optimize the image. In some applications, the relationship between the band-pass filter and z-offset may be known to within a certain degree of accuracy. This is analogous to the situation where variable resistors and capacitors are adjusted simultaneously under a known relationship, which does not have to be linear.

The band-pass filter may be adjusted by digitally controlling variable resistors and capacitors in the filter to achieve the appropriate filter characteristics. In the alternative, a series of band-pass filters can be employed and the filter circuit can switch between different filters; however, this is a more cumbersome approach. On the other hand, while this approach is cumbersome and less ideal in terms of having intervals of filtration, more precise control at a given filtration setting is achievable because it is easier to compensate for variabilities from, for example, changes in resistor and capacitor noise.

As noted above, the polarization controller 216 may be driven, for example, by a step motor 218, to perform polarization sensitive OCT ("PS-OCT"). It should be appreciated by those skilled in the art that this technique is applicable to both spectral domain OCT systems, and to time domain OCT system. Assessing biological tissues such as organized collagen, particularly in tendon, can benefit from having desired control over the polarization of light in the reference arm. As a brief overview of the concept of polarization, polarized light can be viewed as consisting of x- and y-components, with the z-direction being the direction of propagation. The birefringence, which may be used to assess tissue composition, refers to the change in phase of one component relative to the other, such as the x-component relative to the y-component, as the light propagates through the tissue. Some tissues, such as organized collagen in particular, are highly birefringent. Most tissue is not birefringent, however, and tissue that, for example, has lost its collagen organization loses its birefringence. Thus, loss of collagen organization in tendon, even if the tendon looks normal by visual inspection, can be identified by PS-OCT, indicating pathologic changes.

When the x- and y-components are combined in different relative intensities and different phases, the end result can be linearly polarized light of any axis (not just x or y), circularly polarized light (right or left), or elliptically polarized light. The polarization controller 216 may be configured to change the polarization of the light in the reference arm between these polarization states in a controlled, or well-defined, manner. Thus; the polarization controller 216 allows for the sweeping through these polarization states in a manner that can provide the identification of an optimal polarization state for defining tissue organization. The approach may also be designed to insure minimum and maximum in backreflection intensity.

There are two different approaches for performing PS-OCT, single and dual channel. In brief, single detector PS-OCT measures changes in the backreflection of light within tissue as the sample or reference arm polarization state is changed. As it does not depend on recording an absolute value that can change when light propagates through the fibers, or tissue not of interest, but rather an image change as the polarization is changed, it is relatively robust to artifacts and simple to implement. Additional advantages over dual channel approaches are that single channel approaches are minimally susceptible to fiber bending artifacts, are performed in real time, produce results that can be read directly off the screen, and include an optical design that is relatively simple making it less susceptible to internal artifacts such as angular deviation of reflectors and filters.

Some understanding of how single detector PS-OCT is provided by example. With highly birefringent tissue, such as healthy tendon, bands occur in the tissue as a result of rotation of the backreflected light polarization state as it passes through the tissue. In other words, in this unusual circumstance, birefringence assessment does not demand reference arm polarization to be rotated. Rather, the peak-to-peak distance in the image is a measure of birefringence. But for most other tissues relevant to this analysis technique, such as aged or diseased tendon, the birefringence is lower. For these tissues, the distance over which the backreflected light rotates a single cycle is greater than the width of the imaging area; that is, band width is greater than tissue width. So, rather than using a single incident polarization state in the reference and sample arm, the polarization state of reference arm light is rotated, for example, at a constant velocity. A measurement, such as time or change in polarization paddle position, to go from peak-to-peak at a given point in the image with rotation of reference arm polarization is a measure of tissue birefringence. That is, the reference arm is being rotated through a range of polarization states with the polarization controller 216, so that as this is occurs, the backreflection of the sample arm is changing. If the birefringence in the sample or tissue is high, the backreflection in the sample will change rapidly with changes in the reference arm.

As stated, PS-OCT includes tailoring polarization rotation in the reference arm to improve assessment of tissue structure. Again, polarization is rotated between linear, circular, and elliptical states in a controlled manner. By way of example, the polarization controller 216 may be a standard Lefevre type fiber optic polarizer that can be changed at a constant velocity. Such a polarization controller 216 includes a certain length of single mode fiber spooled on three paddles. These paddles are adapted and connected to a driver 218, such as a step motor, that serves as a driver controller of angular position and rates. The driven paddles can be stepwise rotated back and forth within plus or minus ninety degrees, and with 0.9 degree steps, via a programmable motion controller or through a computer processor. The paddle rotation rate is variable and controllable as described below. In a Lefevre type polarization controller, two quarter-wave coils control the ellipticity and a half-wave coil controls the linear orientation. This type of polarization controller may be desirable because it has low polarization mode dispersion ("PMD"), which at higher levels can impair the resolution of an OCT system. Motorization may be added to the polarization controller to allow constant velocity rotation, with each paddle velocity being controlled separately.

Interference is maximum between the reference and sample arm when polarization is completely matched between the two arms. Therefore, if the sample arm contains one polarization state, at maximum interference the polarization of the reference and sample arm are the same. Second, because of this, polarization in the reference arm is determined through the use of polarization filters and retarders, which control phase, such as quarter-wave plates in the sample arm.

As the polarization states is changed, data regarding this change can be plotted on a Poincare's sphere to represent the different polarization states as the paddles are rotated. In a Poincare's sphere, the north pole is right circularly polarized light, while the south is left; the equator represents the different linearly polarized states; and any other position on the surface of the sphere is elliptically polarized light. If a data point is on the surface, attenuation is zero, and when it is inside the sphere a finite amount of attenuation exists from the sample. A sweep of polarization between different states can be plotted and displayed on the sphere. It is contemplated that with this approach, a scanning pattern that optimizes the peaks from troughs during scanning can be determined.

Note that these steps are done to establish the polarization sweep in the reference arm. Once a sweep has been deemed as optimal for the imaging task at hand, the fibers are fixed in position, then paddle positions and motor parameters kept constant. In other words, once the sweep is established, these steps do not need to be repeated. The actual steps to get to this fixed reference arm sweep generally are as follows.

The paddles in the reference arm are moved to a fixed position. The linear polarizer in the sample arm is rotated through zero, ninety, forty-five, and negative forty-five degrees, consecutively. The corresponding interferogram is measured at each position. The linear paddle position is then maintained in the reference arm. A quarter wave plate is inserted into the beam, and the fast axis is aligned at plus or minus forty-five degrees to the linear polarizer to obtain the right and left circular polarization state, respectively. Again, interferograms are measured. The paddles are then moved in the reference arm to different positions and the foregoing measurements are repeated. By way of example, the sweep may be generated in approximately two seconds.

The present invention has been described in terms of one or more preferred embodiments, and it should be appreciated that many equivalents, alternatives, variations, and modifications, aside from those expressly stated, are possible and within the scope of the invention.

The invention claimed is:

1. An optical coherence tomography system comprising:
   a light source configured to produce light to illuminate a sample with the sample light;
   at least one optical path configured to receive at least one of reference light and sample light from the light source and to illuminate a sample with the received sample light;
   a detector in optical communication with the at least one optical path and configured to receive the reference and sample light;
   a processor coupled to the detector and the light source and configured to:
   a) receive a signal from the detector;
   b) determine, from the received signal, an interference signal related to the reference light and the sample light;
   c) receive a calibration signal from the light source;
   d) identify at least one of a series of extrema and a series of crossing values in the received calibration signal;
   e) identify at least one of a series of calibration extrema and a series of calibration crossing values from the received calibration signal and the identified at least one of series of extrema and series of crossing values by performing an interpolation;
   f) calibrate the interference signal using the identified at least one of a series of calibration extrema and series of calibration crossing values; and
   g) reconstruct an image of the sample from the recalibrated interference signal.

2. The optical coherence tomography system as recited in claim 1 in which the processor is configured to:
   e) identify a series of calibration extrema from the identified series of extrema and received calibration signal by performing a first interpolation, and to identify a series of calibration crossing values from the identified series of zero-crossing values and received calibration signal by performing a second interpolation; and
   f) calibrate the interference signal using the identified series of calibration extrema and series of calibration crossing values.

3. The optical coherence tomography system as recited in claim 2 in which the first interpolation performed by the processor in step e) includes a cubic spline interpolation.

4. The optical coherence tomography system as recited in claim 2 in which the second interpolation performed by the processor in step f) includes a substantially linear interpolation.

5. The optical coherence tomography system as recited in claim 1 in which the interpolation performed by the processor in step e) includes at least one of a cubic spline interpolation and a substantially linear interpolation.

6. The optical coherence tomography system as recited in claim 1 in which the light source is configured to produce light over a range of wavelength values.

7. The optical coherence tomography system as recited in claim 6 further comprising an interferometer coupled to the light source and configured to produce the calibration signal as light is swept over the range of wavelength values.

8. The optical coherence tomography system as recited in claim 1 in which the processor is further configured in step d) to perform a global optimization method to search for the estimated series of extrema and series of crossing values.

9. The optical coherence tomography system as recited in claim 8 in which the global optimization method performed by the processor in step d) is a genetic algorithm and step d) further includes:
   d)i) defining a fitness function such that data values in the calibration signal that are near to extrema and crossing values increase a fitness value for extrema and crossing values, respectively;
   d)ii) selecting a first generation; and
   d)iii) selecting a number of values during each successive generation based on their quality measured by the fitness function.

10. The optical coherence tomography system as recited in claim 1 in which the at least one optical path includes a reference path in optical communication with the light source and configured to receive reference light therefrom and a sample path in optical communication with the light source and configured to receive sample light therefrom and to illuminate a sample with the received sample light.

11. The optical coherence tomography system as recited in claim 1 further comprising a logarithmic amplifier in communication with the light source and configured to receive and amplify therefrom a calibration signal, and in which the processor is configured to receive the amplified calibration signal from the logarithmic amplifier.

12. The optical coherence tomography system as recited in claim 1 further comprising at least one of a logarithmic amplifier, a diode, and a transistor in communication with the detector and configured to amplify the signal received therefrom, thereby increasing a dynamic range of the signal, and in which the processor is configured to receive the amplified signal from the at least one of a logarithmic amplifier, a diode, and a transistor.

13. The optical coherence tomography system as recited in claim 1 further comprising:
   a driver; and
   a polarization controller coupled to the driver and in optical communication with the at least one optical path, the polarization controller configured to change at least one of a polarization and an intensity of the at least one of reference light and sample light in the at least one optical path while being driven by the driver.

14. An optical coherence tomography system comprising:
   a light source;
   a detector;
   an interferometer in optical communication with the light source and the detector;
   a logarithmic amplifier in communication with the light source and configured to receive and amplify a calibration signal therefrom;
   a processor in communication with the logarithmic amplifier and the interferometer, the processor being configured to:
      receive a spectral interference signal from the detector;
      receive the amplified calibration signal from the logarithmic amplifier;
      calibrate the received spectral interference signal using the received amplified calibration signal;
      produce an image having at least one of an improved resolution, an improved contrast, and an increased dynamic range from the calibrated spectral interference signal; and
      in which the light source includes an interferometer for producing the calibration signal.

15. The optical coherence tomography system as recited in claim 14 in which the interferometer includes a reference arm and a sample arm, and the reference arm includes a reflector configured to be displaced along an axis substantially perpendicular to the reflector.

16. The optical coherence tomography system as recited in claim 14 further comprising at least one of a logarithmic amplifier, a diode, and a transistor in communication with the detector and configured to amplify a signal received therefrom.

17. An optical coherence tomography system comprising:
   a light source;
   a detector;
   an interferometer in optical communication with the light source and the detector;
   a logarithmic amplifier in communication with the light source and configured to receive and amplify a calibration signal therefrom;
   a processor in communication with the logarithmic amplifier and the interferometer, the processor being configured to:
      receive a spectral interference signal from the detector;
      receive the amplified calibration signal from the logarithmic amplifier;
      calibrate the received spectral interference signal using the received amplified calibration signal;
      produce an image having at least one of an improved resolution, an improved contrast, and an increased dynamic range from the calibrated spectral interference signal; and
      in which the light source is coupled to another interferometer that is in communication with the logarithmic amplifier, and the another interferometer produces the calibration signal from light received from the light source.

18. The optical coherence tomography system as recited in claim 17 in which the interferometer includes a reference arm and a sample arm, and the reference arm includes a reflector configured to be displaced along an axis substantially perpendicular to the reflector.

19. The optical coherence tomography system as recited in claim 17 further comprising at least one of a logarithmic amplifier, a diode, and a transistor in communication with the detector and configured to amplify a signal received therefrom.

20. An optical coherence tomography system comprising:
   a light source;
   a detector;
   an interferometer in optical communication with the light source and the detector;
   a logarithmic amplifier in communication with the light source and configured to receive and amplify a calibration signal therefrom;
   a processor in communication with the logarithmic amplifier and the interferometer, the processor being configured to:
      receive a spectral interference signal from the detector;
      receive the amplified calibration signal from logarithmic amplifier;
      calibrate the received spectral interference signal using the received amplified calibration signal;
      produce an image having at least one of an improved resolution, an improved contrast, and an increased dynamic range from the calibrated spectral interference signal;
      further comprising a band-pass filter in communication with the detector, the band-pass filter being configured to filter a signal received from the detector and in which the band-pass filter is a variable band-pass filter.

21. The optical coherence tomography system as recited in claim 20 in which a passband of the variable band-pass filter is determined using information related to a displacement of the mirror in the reference arm.

22. The optical coherence tomography system as recited in claim 21 in which the mirror in the reference arm is configured to be adjusted with the variable band-pass filter at least one of manually and computationally.

23. An optical coherence tomography system comprising:
a light source;
a detector;
an interferometer in optical communication with the light source and the detector;
a logarithmic amplifier in communication with the light source and configured to receive and amplify a calibration signal therefrom;
a processor in communication with the logarithmic amplifier and the interferometer, the processor being configured to:
receive a spectral interference signal from the detector;
receive the amplified calibration signal from the logarithmic amplifier;
calibrate the received spectral interference signal using the received amplified calibration signal;
produce an image having at least one of an improved resolution, an improved contrast, and an increased dynamic range from the calibrated spectral interference signal; and
in which the processor is configured to calibrate the received spectral interference signal using the received amplified calibration signal by:
i) identifying at least one of a series of extrema and a series of crossing values in the amplified calibration signal;
ii) identifying a series of calibration extrema from the identified series of extrema and amplified calibration signal by performing a first interpolation;
iii) identifying a series of calibration crossing values from the identified series of zero-crossing values and amplified calibration signal by performing a second interpolation; and
iv) calibrating the spectral interference signal using the identified series of calibration extrema and series of calibration crossing values.

24. The optical coherence tomography system as recited in claim 23 in which the interferometer includes a reference arm and a sample arm, and the reference arm includes a reflector configured to be displaced along an axis substantially perpendicular to the reflector.

25. The optical coherence tomography system as recited in claim 23 further comprising at least one of a logarithmic amplifier, a diode, and a transistor in communication with the detector and configured to amplify a signal received therefrom.

26. An optical coherence tomography system comprising:
a light source;
a detector;
an interferometer in optical communication with the light source and the detector;
a logarithmic amplifier in communication with the light source and configured to receive and amplify a calibration signal therefrom;
a processor in communication with the logarithmic amplifier and the interferometer, the Processor being configured to:
receive a spectral interference signal from the detector;
receive the amplified calibration signal from the logarithmic amplifier;
calibrate the received spectral interference signal using the received amplified calibration signal;
produce an image having at least one of an improved resolution, an improved contrast, and an increased dynamic range from the calibrated spectral interference signal; and
in which the processor is further configured to identify the series of calibration extrema and series of calibration crossing values by performing a global optimization method.

27. The optical coherence tomography system as recited in claim 26 in which the interferometer includes a reference arm and a sample arm, and the reference arm includes a reflector configured to be displaced along an axis substantially perpendicular to the reflector.

28. The optical coherence tomography system as recited in claim 26 further comprising at least one of a logarithmic amplifier, a diode, and a transistor in communication with the detector and configured to amplify a signal received therefrom.

29. A method for producing an image of a subject with an optical coherence tomography (OCT) system, the steps comprising:
a) illuminating at least one of a reference path of the OCT system and a sample path of the OCT system with a light source, the sample path being in optical communication with the subject;
b) identifying an interference signal from the reference and sample paths of the OCT system;
c) acquiring a calibration signal from light emitted by the light source;
d) estimating a series of extrema and a series of crossing values from the acquired calibration signal;
e) identifing a first series of calibration characteristics from the estimated series of extrema and amplified calibration signal by performing a first interpolation;
f) identifying a second series of calibration characteristics from the estimated series of crossing values and amplified calibration signal by performing a second interpolation;
g) calibrating the interference signal using at least one of the identified first and second series of calibration characteristics;
h) reconstructing an image of the subject using the calibrated interference signal; and
further comprising the step of logarithmically amplifying the calibration signal to produce an amplified calibration signal, and in which the series of extrema estimated in step d) are estimated from the amplified calibration signal.

30. A method for producing an image of a subject with an optical coherence tomography (OCT) system, the steps comprising:
a) illuminating at least one of a reference path of the OCT system and a sample path of the OCT system with a light source, the sample path being in optical communication with the subject;
b) identifying an interference signal from the reference and sample paths the OCT system;
acquiring a calibration signal from light emitted by the light source;
d) estimating a series of extrema and a series of crossing values from the acquired calibration signal;

e) identifying a first series of calibration characteristics from the estimated series of extrema and amplified calibration signal by performing a first interpolation;

f) identifying a second series of calibration characteristics from the estimated series of crossing values and amplified calibration signal by performing a second interpolation;

g) calibrating the interference signal using at least one of the identified first and second series of calibration characteristics;

h) reconstructing an image of the subject using the calibrated interference signal; and further comprising the step of logarithmically amplifying the interference signal before calibrating the interference signal to increase a dynamic range of the interference signal.

31. The method as recited in claim 30 in which step a) includes producing the wavelength of the light over a range of wavelength values.

32. The method as recited in claim 31 in which step c) includes illuminating an interferometer as the light source produces the wavelength of the light over the range of wavelength values in step a).

33. The method as recited in claim 30 in which step d) includes performing a global optimization method to search for the at least one of the estimated series of extrema and series of crossing values.

34. The method as recited in claim 33 in which the global optimization method in step d) is a search technique incorporating at least one of a genetic algorithm and an artificial intelligence modality, and step d) further includes:

d)i) determining a fitness function such that data values in the calibration signal that are near to the at least one of the extrema and crossing values increase a fitness value for the at least one of the extrema and crossing values, respectively;

d)ii) selecting a first generation; and d)iii) selecting a number of values during each successive generation based on their quality measured by the fitness function.

35. The method as recited in claim 30 in which at least one of the series of calibration characteristics includes at least one of zero-crossing values and DC-crossing values.

36. The method as recited in claim 30 in which the first interpolation performed in step e) includes at least one of a cubic spline interpolation, a Gaussian interpolation, and a polynomial interpolation.

37. The method as recited in claim 30 in which the second interpolation performed in step f) includes one of a linear interpolation, a Gaussian interpolation, a polynomial interpolation, and spline interpolation.

38. The method as recited in claim 30 in which the first and second series of calibration characteristics are distributed substantially uniformly along at least one of an abscissa and an ordinate.

39. The method as recited in claim 38 in which the at least one of the abscissa and the ordinate represents at least one of wavelength and wavenumber.

40. The method as recited in claim 30 in which step g) includes forming a calibrated signal array from those values in the interference signal associated with at least one of the first and second series of calibration characteristics.

* * * * *

UNITED STATES PATENT AND TRADEMARK OFFICE
CERTIFICATE OF CORRECTION

PATENT NO.      : 9,506,740 B2                                          Page 1 of 1
APPLICATION NO. : 13/513052
DATED           : November 29, 2016
INVENTOR(S)     : Brezinski et al.

It is certified that error appears in the above-identified patent and that said Letters Patent is hereby corrected as shown below:

In the Specification

Column 16, Line 25 - delete "("AID")" and insert -- ("A/D") --

In the Claims

Column 22, Line 55 Claim 20 - delete "from logarithmic" and insert -- from the logarithmic --

Column 24, Line 61 Claim 30 - delete "path the" and insert -- paths of the --

Signed and Sealed this
Twenty-eighth Day of March, 2017

Michelle K. Lee
*Director of the United States Patent and Trademark Office*